United States Patent [19]

Rich

[11] Patent Number: 4,730,055

[45] Date of Patent: Mar. 8, 1988

[54] METHOD FOR SILYLATING AROMATIC IMIDES AND SILYLIMIDES MADE THEREFROM

[75] Inventor: Jonathan D. Rich, Rexford, N.Y.

[73] Assignee: General Electric Company, Schenectady, N.Y.

[21] Appl. No.: 902,813

[22] Filed: Sep. 2, 1986

Related U.S. Application Data

[63] Continuation-in-part of Ser. No. 647,301, Aug. 30, 1984, abandoned.

[51] Int. Cl.$^4$ .............................. C07F 7/10; C07F 7/16; C07F 7/18
[52] U.S. Cl. ........................................................ 548/406
[58] Field of Search ......................................... 548/406

[56] References Cited

U.S. PATENT DOCUMENTS

| 2,474,087 | 6/1949 | Barry et al. | 556/468 |
| 2,598,434 | 5/1952 | Mohler et al. | 556/468 |
| 3,746,732 | 7/1973 | Atwell et al. | 556/9 |
| 3,772,347 | 11/1973 | Atwell et al. | 556/468 |
| 4,196,139 | 4/1980 | Seiler et al. | 556/481 |
| 4,474,976 | 10/1984 | Faltynek | 556/481 |

FOREIGN PATENT DOCUMENTS 2164040  3/1986  United Kingdom ............... 548/406

OTHER PUBLICATIONS

Matsumoto et al., The Reaction of Hexamethyldisilane with Dihalonitrobenzene in the Presence of Tetrakis(triphenylphosphine)palladium(O), Synthesis of Bis(trimethylsilyl)nitrobenzenes and (Trimethylsilyl)chloronitrobenzenes, J. Organometallic Chemistry, 208, 145-152, (1981).
Synthesis of Some Methyldisilanes Containing Functional Groups, Kumada et al., J. Org. Chem., 21, 1264-1268, (1956).
Further Studies on Reactions of Organic Halides with Disilanes Catalysed by Transition Metal Complexes, Eaborn et al., J. Organometallic Chemistry, vol. 225, pp. 331-341, (1982).
Derwent Abstracts, Toshiba Silicone KK, 3/26/76, Japan, 033409.
Silicon-Carbon Bond Formation by the Reaction of Disilanes with Halobenzenes in the Presence of Tetrakis(triphenylphosphine)palladium(O), Matsumoto et al., J. of Organometallic Chemistry 85, pp. $C_1$-$C_3$, (1975).
Preparation of Dimethyltetramethoxydisilane from the Disilane Fraction, Watanabe, J. of Organometallic Chemistry, 128, pp. 173-175, (1977).
Preparation of Substituted Benzoyltrimethylsilanes by the Palladium-Catalyzed Silylation of Substituted Benzoyl Chlorides with Hexamethyldisilane, Yamamoto, Tetrahedron Letters, vol. 21, pp. 1653-1656, (1980).
Tetrakis(triphenylphosphine)Palladium(O), Coulson, Inorganic Syntheses, pp. 121-124.
K. P. C. Vollhardt/Z. Y. Yang, "Nickel-Catalyzed Reduction of Carbon Monoxide by Hexamethyldisilane: A New Reaction Leading To A Novel Synthesis of Siloxanes", Angew. Chem. Inc. Ed. Engl. 23, No. 6, (1984), pp. 460–461.
H. Matsumoto/S. Koike/I. Matsubara/T. Nakano/Y. Nagai, "A New Reductive Silylation of p-quinones with Hexamethyldisilane Catalyzed by Iodine", Chem. Lett., (Eng.), 4, (1982), pp. 533–534, Chemical Abstracts, vol. 97, 38986s, (1982).
Hopff et al., Chemical Abstracts, vol. 68, 106060p, (1968).
Sagami Chemical Research, Chemical Abstracts, vol. 101, 38214q, (1984).
Hopff et al., Chemical Abstracts, vol. 73, 4248s, (1970).
Sagami Chemical Research, Chemical Abstracts, vol. 101, 72, 944n, (1984).
Pebalk et al., Chemical Abstracts, vol. 90, 6797v, (1979).
Korshak et al., Chemical Abstracts, vol. 78, 4713t, (1973).

*Primary Examiner*—Donald G. Daus
*Assistant Examiner*—Diana G. Rivers
*Attorney, Agent, or Firm*—William A. Teoli; Davis, Jr. James C.; James Magee, Jr.

[57] ABSTRACT

A method is provided for silylating aromatic imides by effecting reaction between a polysilane and such aromatic imide in the presence of an effective amount of a catalyst of a transition metal such as palladium.

13 Claims, No Drawings

METHOD FOR SILYLATING AROMATIC IMIDES AND SILYLIMIDES MADE THEREFROM

CROSS REFERENCE TO RELATED APPLICATIONS

This application is a continuation-in-part of copending application Ser. No. 647,301, filed Aug. 30, 1984, now abandoned.

Reference also is made to copending application Ser. No. 765,089, filed Aug. 13, 1985, for "Silylation Method and Silanes Made Therefrom", assigned to the same assignee as the present invention and incorporated herein by reference.

BACKGROUND OF THE INVENTION

As shown by Barry et al, U.S. Pat. No. 2,474,087, disilanes have been used to make organosilanes by reacting halogenated organic compounds, such as alkyl halides or aryl halides, with halodisilane in the presence of a metallic catalyst. A somewhat similar procedure is shown in U.S. Pat. No. 3,772,347, Atwell et al, employing a halogenated disilane and an organic chloride such as chlorobenzene or butyl chloride to produce the appropriate organohalosilane.

Transition metal catalyzed silylation of activated aromatic substrate with polysilane can sometimes be less predictable. It has been found that the nature of the activating group on the aromatic nucleus can enhance or interfere with the nuclear silylation. For example, as shown by Matsumoto et al., JOMC 85, Cl (1985), nitrochlorobenzene can be readily silylated with disilane. Experience has shown, however, that the silylation of carbonyl substituted aromatic compounds with polysilane is often not feasible, since disilanes are well-known reducing agent for carbonyl groups. For example, conversion of aromatic aldehyde to alcohol is shown by Japanese Patent No. 5942391. Reductive silylation of p-quinone is shown by Matsumoto et al., Chem. Lett. 4 (1982) pp. 533–4. The silylation of certain functionalized aromatic dicarbonyl compounds, such as chlorophthalic anhydride with disilane also is not feasible.

An additional factor in predicting ease of silylation of aromatic substrates with polysilanes is the nature of the monovalent radicals of the polysilane attached to silicon. In some cases, for example, aromatic substrates are more readily silylated with polysilane having monovalent hydrocarbon radicals attached to silicon, such as hexamethyl disilane, than polysilane having one or more functional groups attached to silicon, such as halogen or alkoxy. The preferred monovalent functional groups attached to silicon are methoxy, ethoxy, propoxy, butoxy and pentoxy, or a phenoxy group, and chloro, as well as a mixture thereof.

The present invention is based on the discovery that unlike carbonyl substituted aromatic compounds, such as halogenated aromatic anhydrides, other functionalized aromatic dicarbonyl compounds, such as halogenated aromatic imides, for example, chlorophthalimide, can be readily silylated with polysilanes including polysilanes substituted with functional groups, such as halogen and alkoxy. As a result, the present invention provides for the synthesis of silylaromatic imides in accordance with the following equation:

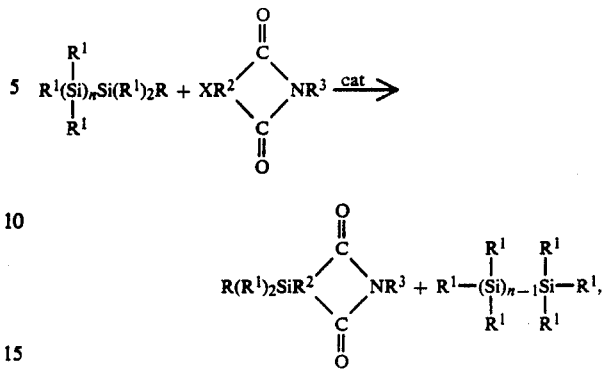

where X is halogen, R is a monovalent radical selected from the class of X, hydrogen, $C_{(1-8)}$ alkoxy, $C_{(1-13)}$ hydrocarbon and substituted $C_{(1-13)}$ hydrocarbon, $R^1$ is selected from R, —O— and —S—, and when $R^1$ is —O— or —S— or a mixture thereof, $R^1$ can form

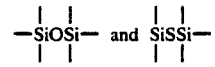

connecting groups, $R^2$ is a trivalent $C_{(6-13)}$ aromatic organic radical, $R^3$ is selected from $C_{(1-13)}$ monovalent hydrocarbon and $C_{(1-13)}$ monovalent hydrocarbon radicals substituted with neutral radicals, and n is an integer having a value of from 1 to 50 inclusive.

STATEMENT OF THE INVENTION

There is provided by the present invention a method for making silyl aromatic imides of the formula

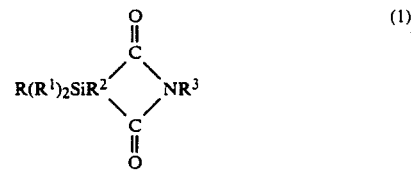

which comprises
(A) effecting reaction between a polysilane of the formula

and a haloaromatic imide of the formula,

in the presence of an effective amount of a transition metal catalyst, and
(B) recovering the resulting silyl aromatic imide from the mixture of (A), where R, R¹, R², R³, n and X are as previously defined.

Radicals which are included within R and R¹ of formulas (1) and (2) are, for example, hydrogen, halogen, such as chloro, bromo; $C_{(1-8)}$ alkoxy, for example, methoxy, ethoxy, propoxy; $C_{(1-8)}$ alkyl, such as methyl, ethyl, propyl, butyl, pentyl; aryl radicals and haloaryl radicals such as phenyl, tolyl, xylyl, naphthyl, chlorophenyl,; alkenyl radicals such as vinyl, allyl; haloalkyl radicals such as trifluoropropyl, etc.

Radicals which are included within R² of formulas (1) and (3) are, for example,

, etc.

Radicals included within R³ of formulas (1) and (3) are, for example, $C_{(1-8)}$ alkyl radicals and $C_{(6-13)}$ aryl radicals included within R.

Among the haloaromatic imides of formula (1) there are included, for example, N-butyl-3-chlorophthalimide, N-butyl-4-chlorophthalimide, N-phenyl-3-chlorophthalimide, N-phenyl-4-chlorophthalimide, etc.

Among the polysilanes shown by formula (2) there are included hexamethyldisilane, chloropentamethyldisilane, 1,2-dichlorotetramethyldisilane, 1,1,2-trichlorotrimethyldisilane, 1,1,2,2-tetrachlorodimethyldisilane, hexachlorodisilane, methoxypentamethyldisilane, 1,2-dimethoxytetramethyldisilane, ethoxypentamethyldisilane, 1,2-diethoxypentamethyldisilane, etc.

Also encompassed by the present invention, are certain silyl aromatic imides included within formula (1). These silyl aromatic imides are shown by the following formula,

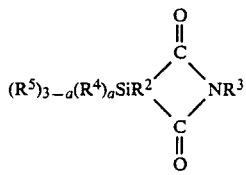 (4)

where R² and R³ are as previously defined. R⁴ is a $C_{(1-14)}$ monovalent hydrocarbon radical or $C_{(1-14)}$ monovalent hydrocarbon radical substituted with radicals neutral during silylation such as nitro, chloro, cyano, or mixtures thereof, R⁵ is selected from halogen, —OR⁴, or a mixture thereof, and a is a whole number having a value of 0 to 2 inclusive. Radicals included within R⁴ are, for example, methyl, ethyl, propyl, butyl, pentyl, hexyl, heptyl, octyl, phenyl, xylyl, tolyl, naphthyl, or mixtures thereof which can be substituted with one or more halogen radicals such as chloro, fluoro, bromo, such as trifluoro propyl, chlorophenyl as well as nitrophenyl. Radicals included within R⁵ are, for example, chloro, bromo, fluoro, methoxy, propoxy, butoxy, pentoxy, phenoxy, and mixtures thereof.

The silyl aromatic imides of formula (4) can provide imide disiloxanes having the formula,

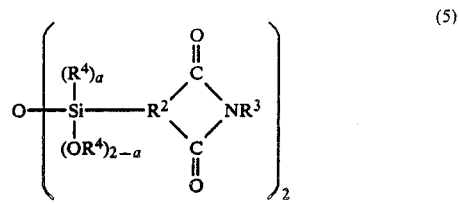 (5)

where R², R³, R⁴, R⁵ and a are as previously defined. The silyl aromatic imides of formula (4) and imide disiloxanes of formula (5) are useful as thermally resistant adhesion promoters.

Transition metal catalysts which can be employed in the practice of the present invention are, for example, palladium, Pd/C, tetrakis(triphenylphosphine)palladium, bis(benzonitrile)palladium dichloride, bis(triphenylphosphine)palladium dichloride, etc.

An effective amount of transition metal catalyst means there can be utilized from 0.01 to 0.10 part of transition metal catalyst based on the weight of the halodicarbonyl compound of formula (1).

In the practice of the invention, reaction is effected between the haloaromatic imide of formula (3) and the polysilane of formula (2) in the presence of an effective amount of a transition metal catalyst as previously defined. Experience has shown that effective results can be obtained if the reaction is carried out in an inert gas atmosphere, for example, nitrogen, argon, or other noble gases. The proportions of the haloaromatic imide and the polysilane can vary widely. However, it is preferred to utilize a sufficient amount of polysilane to provide at least 2 gram atoms of silicon, per mole of the haloaromatic imide.

The use of an inert organic solvent for example, toluene, anisole, xylene, mesitylene, can be used to facilitate the reaction between the polysilane and the aromatic halide. Temperatures of from 110° C. to 300° C. can be employed. The recovery of the desired silyl aromatic imide can be achieved in accordance with standard techniques such as precipitation by addition of a nonpolar solvent, for example, hexane, followed by filtration and removal of the solvent in vacuo.

The silyl aromatic imides of the present invention are useful as adhesion promoters for RTV formulations and intermediates for making the corresponding silyl aromatic anhydrides such as 1,3-bis(phthalic anhydride)-disiloxane by standard alkaline hydrolysis procedures.

In order that those skilled in the art will be better able to practice the present invention, the following examples are given by way of illustration and not by way of limitation. All parts are by weight.

EXAMPLE 1

A solution of 20 ml of toluene containing 1.26 grams (5.62 millimoles) of N-n-butyl-4-chlorophthalimide and 2.0 grams (1.12 millimoles) of 1,2-dimethoxytetramethyldisilane and 40 milligrams (5 mole percent) of tetrakistriphenylphenylphosphine palladium was heated under argon to reflux. The refluxing solution turned to a golden yellow and then to a deep red color. After refluxing for 48 hours, the mixture was allowed to cool and it was stripped of organic solvent. The residue was then purified by adding 30 ml of dry hexane. Residue was removed by filtration followed by removal of the solvent in vacuo. There was obtained an 83% yield of 4-(dimethylmethoxysilyl)-N-n-butylphthalimide. The identity of the product was further confirmed by mass spectral gas chromatographic analysis.

The material was subjected to silica gel chromatography with hexane elution which resulted in hydrolysis of the initially formed methoxysilane to yield the corresponding bisimide having the formula

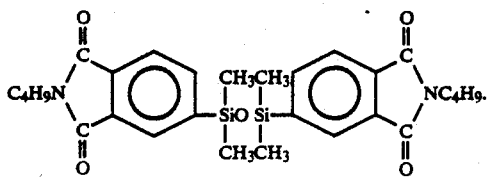

This bisimide is useful as a silicone RTV adhesion promoter.

EXAMPLE 2

The procedure of Example 1 was repeated, except there was used 0.2 grams of N-methyl-4-chlorophthalimide, 0.37 grams of 1,2-dimethoxytetramethyldisilane and 40 milligrams of $(Ph_3P)_4Pd$. The solution was heated with stirring for 15 hours resulting in a 55% yield of N-methyl-4-(dimethylmethoxysilyl)phthalimide.

EXAMPLE 3

A reaction mixture containing 98 g (0.43 moles) of N-methyl-4-chlorophthalimide and 93 g (0.44 moles) of sym-tetramethoxydimethyldisilane was heated neat to 145° C. in the presence of 1 mole % tetrakis(triphenylphosphine)palladium. After 24 hours, 57 g of methyltrimethoxysilane was obtained. Vacuum distillation gave 19 g of N-methyl-4-dimethoxymethylsilylphthalimide (b.p. 160/0.1 torr).

EXAMPLE 4

A reaction scheme is designed whereby 27 g (0.11 moles) of hexamethoxydisilane and 21 g (0.11 g) of N-methyl-4-chlorophthalimide are reacted together at 145° C. under nitrogen in the presence of 1 mole % tetrakis(triphenylphosphine)palladium. Subsequent vacuum distillation yields the desired compound N-methyl-4-trimethoxysilylphthalimide.

EXAMPLE 5

A reaction mixture containing 5 gm (0.021 moles) of n-butyl-4-chlorophthalimide and 3.95 gm (0.021 moles) of 1.2 dichlorotetramethyldisilane dissolved in 10 ml of o-xylene was heated to 150° C. in the presence of 5 mole % tetrakis(triphenylphosphine)palladium. After 24 hours reaction time, GC and GC/MS analysis showed a 24% yield of N-butyl-4-chlorodimethylsilyl-phthalimide. The product is readily isolatable by vacuum distillation.

EXAMPLE 6

The procedure was carried out as described in Example 5 except that 4.1 gm (0.021 moles) of N-methyl-4-chlorophthalimide were employed rather than N-butyl-4-chlorophthalimide. The yield of N-methyl-4-chlorodimethylsilylphthalimidephthalimide was 21%.

EXAMPLE 7

A reaction mixture containing 4.1 gm (0.021 moles) of N-methyl-4-chlorophthalimide and 4.8 gm (0.021 moles) of sym-tetrachlorodimethyldisilane in o-xylene solvent is heated to reflux temperature for 24 hours in the presence of 1 mole % palladium on silica catalyst. Vacuum distillation at 168°/0.1 torr provides N-methyl-4-dichloromethylsilylphthalimide. It is a white crystalline solid m.p. 89°-94° C. nmr(CCl$_4$, CH$_2$Cl$_2$ ref) δ 8.16 (S, 1H, Arom H$_3$) δ 8.05 (d, 1H, J-10 Hz, Arom H$_6$) δ 7.78 (d. 1H, J-10 Hz, Arom H$_5$) δ 3.11 (S, 3H, N—CH$_3$) δ 1.07 (S, 3H, Si—CH$_3$) mass spec calc. 272.9779 obs. 272.9776.

Although the above examples are directed to only a few of the very many variables which can be utilized in the practice of the present invention, it should be understood that the present invention is directed to the use of a much broader variety of aromatic halophthalimides of formula (3) and a disilane of formula (2) in the presence of a wider variety of transition metal catalysts as shown in the description preceding these examples.

What I claim as new and desire to secure by Letters Patent of the United States is:

1. A method for making silyl aromatic imides of the formula

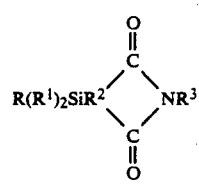

which comprises
(A) effecting reaction between a polysilane of the formula

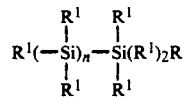

and a haloaromatic imide of the formula,

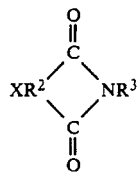

in the presence of an effective amount of a transition metal catalyst, and
(B) recovering the resulting silyl aromatic imide from the mixture of (A),
where X is halogen, R is a monovalent group selected from the class of X, hydrogen, C$_{(1-8)}$ alkoxy, C$_{(1-13)}$ hydrocarbon groups and C$_{(1-13)}$ hydrocarbon groups substituted with radicals neutral during silylation, R$^1$ is selected from R, —O— and —S—, and when R$^1$ is —O— or —S— or a mixture thereof, R$^1$ can form ≡Si-OSi≡ or ≡SiSSi≡, connecting groups, R$^2$ is a trivalent C$_{(6-13)}$ aromatic organic group, R$^3$ is selected from C$_{(1-13)}$ monovalent hydrocarbon groups and monovalent hydrocarbon groups substituted with radicals neutral during silylation, and n is an integer having a value of from 1 to 50 inclusive.

2. A method in accordance with claim 1, where the disilane is dimethoxytetramethyldisilane.

3. A method in accordance with claim 1, where the transition metal catalyst is tetrakis-triphenylphenylphosphene palladium.

4. A method in accordance with claim 1, where the chloro phthalimide is N-n-butyl-4-chlorophthalimide.

5. Silyl aromatic imides of the formula,

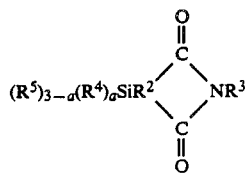

where $R^2$ is a trivalent $C_{(6-13)}$ aromatic organic group, $R^3$ is selected from $C_{(1-13)}$ monovalent hydrocarbon groups and $C_{(1-13)}$ monovalent hydrocarbon groups substituted with radicals neutral during silylation, $R^4$ is $C_{(1-14)}$ monovalent hydrocarbon group, or a $C_{(1-14)}$ monovalent hydrocarbon group substituted with radicals neutral during silylation, $R^5$ is a monovalent group selected from halogen or —$OR^4$, and a is a whole number having a value of 0 to 2 inclusive.

6. 4-(Dimethylmethoxysilyl)N-n-butyl phthalimide.

7. Imide disiloxanes having the formula

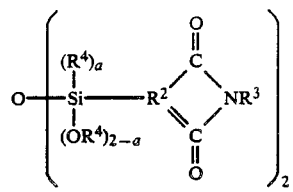

where $R^2$ is a trivalent $C_{(6-13)}$ aromatic organic group, $R^3$ is selected from $C_{(1-13)}$ monovalent hydrocarbon groups and $C_{(1-13)}$ monovalent hydrocarbon groups substituted with radicals neutral during silylation, $R^4$ is $C_{(1-14)}$ monovalent hydrocarbon group or a $C_{(1-14)}$ monovalent hydrocarbon group substituted with radicals neutral during silylation, and a is a whole number having a value of 0 to 2 inclusive.

8. The compound

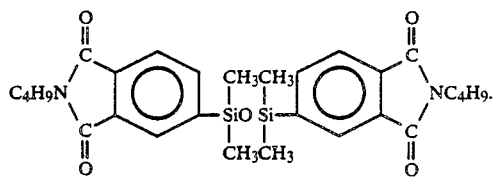

9. N-methyl-4-dimethoxymethylsilylphthalimide.
10. N-methyl-4-trimethoxysilylphthalimide.
11. N-butyl-4-Chlorodimethylsilylphthalimide.
12. N-methyl-4-Dichloromethylsilylphthalimide.
13. N-methyl-4-dimethylmethoxysilylphthalimide.

* * * * *